(12) United States Patent
DeLegge et al.

(10) Patent No.: US 7,582,109 B2
(45) Date of Patent: Sep. 1, 2009

(54) THERMAL TRANSITION METHODS AND DEVICES

(76) Inventors: Rebecca DeLegge, 2356 Darts Cove Way, Mount Pleasant, SC (US) 29466; Michael S. Kitchen, 728 Willowlake Rd., Charleston, SC (US) 29412

( * ) Notice: Subject to any disclaimer, the term of this patent is extended or adjusted under 35 U.S.C. 154(b) by 741 days.

(21) Appl. No.: 11/196,891

(22) Filed: Aug. 4, 2005

(65) Prior Publication Data

US 2006/0030933 A1 Feb. 9, 2006

Related U.S. Application Data

(60) Provisional application No. 60/598,920, filed on Aug. 4, 2004, provisional application No. 60/627,302, filed on Nov. 12, 2004, provisional application No. 60/664,362, filed on Mar. 23, 2005.

(51) Int. Cl.
*A61F 2/06* (2006.01)
*F01B 29/10* (2006.01)

(52) U.S. Cl. .................. 623/1.19; 623/1.18; 60/527; 60/529

(58) Field of Classification Search .................. 623/1.1, 623/1.16, 1.18, 1.19, 1.2, 11, 12; 128/1, 128/341; 60/527, 529
See application file for complete search history.

(56) References Cited

U.S. PATENT DOCUMENTS

| | | | |
|---|---|---|---|
| 4,512,338 A * | 4/1985 | Balko et al. ................. | 606/108 |
| 5,428,123 A | 6/1995 | Ward et al. | |
| 5,506,300 A | 4/1996 | Ward et al. | |
| 5,589,563 A | 12/1996 | Ward et al. | |
| 5,756,632 A | 5/1998 | Ward et al. | |
| 5,814,705 A | 9/1998 | Ward et al. | |
| 5,846,247 A * | 12/1998 | Unsworth et al. ........... | 606/108 |
| 6,458,153 B1 | 10/2002 | Bailey et al. | |
| 6,616,675 B1 | 9/2003 | Evard et al. | |
| 6,620,122 B2 | 9/2003 | Stinson et al. | |
| 6,666,880 B1 * | 12/2003 | Chiu et al. .................. | 623/1.11 |
| 6,682,521 B2 * | 1/2004 | Petrakis .................... | 604/890.1 |
| 6,872,433 B2 * | 3/2005 | Seward et al. ............... | 428/36.9 |
| 2002/0133190 A1 * | 9/2002 | Horton et al. ................ | 606/194 |
| 2002/0169466 A1 | 11/2002 | Peterson et al. | |
| 2003/0069533 A1 | 4/2003 | Kakutani et al. | |
| 2004/0073155 A1 | 4/2004 | Laufer et al. | |
| 2004/0267290 A1 | 12/2004 | Baker et al. | |
| 2005/0056292 A1 | 3/2005 | Cooper | |

OTHER PUBLICATIONS

Calo•MER™ Shape-Memory Thermoplastic, pp. 1-4 Website: www.polymertech.com/materials/calomer.html (Apr. 8, 2003).

\* cited by examiner

*Primary Examiner*—Thomas E Denion
*Assistant Examiner*—Christopher Jetton
(74) *Attorney, Agent, or Firm*—B. Craig Killough (57) ABSTRACT

A method of sequentially transitioning a thermally active shape memory device progressively translocates the thermally active shape memory device through a first controlled temperature zone and through an additional controlled temperature zone. The thermally active shape memory device is thermally transitioned and changed in geometric shape as a result of thermal communication of the shape memory device with either or both of the controlled temperature zones to produce a transitioned thermally active shape memory device. Novel devices produced according to the method are also disclosed.

14 Claims, 12 Drawing Sheets

THERMAL TRANSITION METHODS AND DEVICES

Applicant claims the benefit of U.S. Provisional Application Ser. No. 60/598,920 filed Aug. 4, 2004.

Applicant claims the benefit of U.S. Provisional Application Ser. No. 60/627,302 filed Nov. 12, 2004.

Applicant claims the benefit of U.S. Provisional Application Ser. No. 60/664,362 filed Mar. 23, 2005.

FIELD OF THE INVENTION

This invention relates to temperature dependent transition of shape memory materials.

BACKGROUND OF THE INVENTION

Shape memory materials (particularly those of nitinol and various nitinol like alloys) have physical properties that may be varied dependent upon the temperature of the immediate environment in which the memory device exists. For nitinol alloys two forms are described: Martensite, which is the low temperature form generally may be thought of as a malleable metal; and Austenite, a high temperature form which exhibits properties of shape memory and super-elasticity. The transition between two forms of nitinol is characterized by a hysteresis curve which is defined by complete transition to martensite form ($M_f$) at the lower end of the temperature range and complete transition to austenite ($A_f$) at the higher end of temperature range. The upper and lower limits of and breadth of this range depend upon alloy composition of the shape memory material and upon work performed on the device in the manufacturing process.

Alloys are available with $M_f$ temperatures above 0 degrees centigrade and $A_f$ temperatures below 37 degrees centigrade; devices with these characteristics may be positioned at temperatures at or below $M_f$ and deployed by heating to temperature ranges equal to or greater than $A_f$. There is a need to be able to reliably deploy a device composed of shape memory material with a hysteresis curve within this defined range into the human or mammalian body.

Current methods of stent placement invariably involve introduction of a pre-formed stent across an obstructing lesion with limitation in the size and geometry of the stent mandated by its final form as the devices must be placed with a size nearly as great as their final deployed size. Current stents may be expanded to a limited degree with balloon instrumentation however expansion is limited to less than a fifty percent increase over the placement dimension, furthermore the capacity for balloon expansion comes at the cost of having the stent proper composed of a relatively malleable material which may be subject to compression and re-stenosis with expansion of the obstructing lesion over time.

Multiple current systems exist and are in development for stenting in vascular and coronary artery disease states. Typical applications include use of uniform cross-section tubular stents for stenotic peripheral vascular lesions and most commonly for coronary artery lesions. Instrumentation techniques for these lesions typically involve introduction of a balloon across an obstructing lesion, inflation of the balloon affecting dilatation of the obstruction, followed by placement and release of a mechanically trapped stent across the lesion. While these techniques and devices have afforded good clinical results, there remain limitations in anatomic locations where stents may be placed and the precision with which they may be positioned.

Relative size of pre-deployment and post deployment shapes likewise becomes a limiting factor in use of currently available stent designs and placement techniques. There is a need for stent type devices that can be placed and precisely positioned across access lumens that are markedly smaller than the relative size of the deployed device or through convoluted routes of access that render placement of current devices technically difficult.

Billiary system disease often presents with symptoms of stenosis and or obstruction. Historically a number of techniques have been developed to affect decompression or drainage of an obstructed billiary tract; these techniques have varied from open surgical techniques to percutaneous drainage utilizing radiographic localization to a number of endoscopic techniques utilizing balloon dilatation and or plastic and metal stents.

Limitations of current techniques are largely due to re-obstruction secondary to overgrowth of tumor, accumulation of "bio-film", or mechanical failure of the device maintaining patency for billiary drainage. Furthermore, current systems are either permanent in placement or replaced only with extreme difficulty.

Current stent designs accommodate differing sizing needs through a system of individual stents each of differing lengths. The operator must accurately choose the appropriate length of stent based upon information that cannot be directly measured; of necessity sizing information is gathered indirectly with fluoroscopic imaging or direct visualization through an endoscope with both methods subject to inaccuracies. Further, this system requires that an endoscopy suite must stock a large inventory of stents to meet patient requirements. No current billiary stenting systems are available having variable length capabilities.

SUMMARY OF THE INVENTION

The method of thermal deployment described herein provides for controlled, ordered and sequential transition of a shape memory device through creating a line of demarcation between multiple temperature zones, each temperature zone selected corresponding to the two alternate temperature states ($T<M_f$ and $T>A_f$) of a shape memory device. The method provides for controlled physical translocation of the shape memory device between the temperature zones, with transition occurring at the interface between the differing temperatures. The transition occurs in a spatially defined area, which has physical capabilities of providing complete control and separation between the differing temperature zones, while permitting the passage of the shape memory device.

This method may be utilized for stent designs. The relatively small size of the placement catheter the ability to place the catheter across a small lumen provides applications that have previously been unavailable. These devices may range in size, for example, from less than 1.0 millimeter in diameter to in excess of 10 centimeters. The design provides for geometries of single helical design as well as multi-helical designs. The placement technique provides for individual placement of the helices with potential for helical/anti-helical pairs or potentially a plurality of helices placed individually to obtain a final construct. Further geometric consideration is given to variable cross-sectional sizing along the length of the stent permitting conformation to anatomic needs and allowing formation of "anchoring" segments to facilitate placement. Specific geometries for variable geometry type stents include "spool" shaped devices having enlarged cross-sections at proximal and distal ends, tapered or funnel shaped devices with one end tapered towards the other, and spindle shaped devices with mid sections of greater diameter than the ends.

DESCRIPTIONS OF THE PREFERRED EMBODIMENTS

Figure 1:
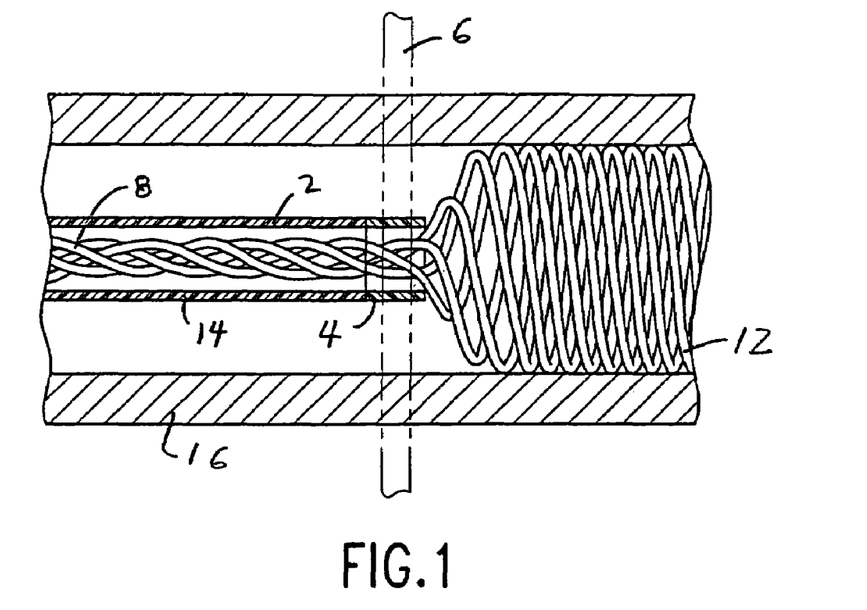
FIG. 1 is a partial, sectioned view of a shape memory device being thermally transitioned in an application.

In the preferred embodiment, differing temperature environments are created and thermally isolated. The shape memory device undergoing transition is spatially translocated between a first temperature zone 2 and a second temperature zone 4. FIG. 1. Transition of the geometry of the shape memory material device 8 occurs in a spatially defined zone 6. The transitioned shape memory device 12 exits the thermal activation device 14 after transition. Once the device has undergone transition its temperature remains at or above (or below) the limits of transition so that there is no uncontrolled return to alternate temperature form. The transition occurs with the thermal activation device in situ so that the transitioned thermally active device is in position for use. As shown, the transitioned thermal activation device is present in a lumen 16. Other in situ applications for the process exist.

Figure 2:
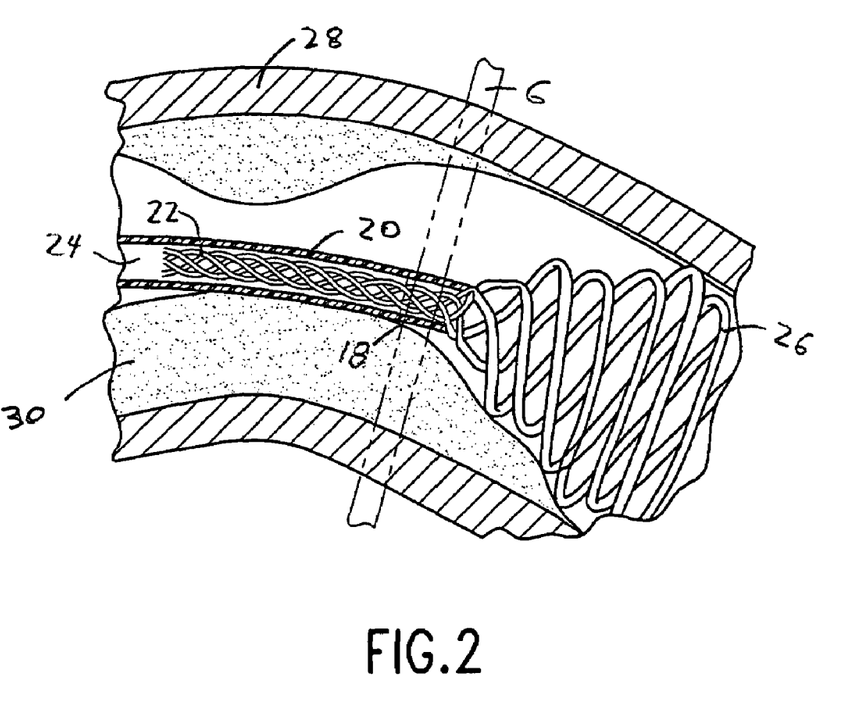
FIG. 2 is a partial, sectioned view of a helical stent being deployed in an anatomical lumen with pathologic stenosis.

The method utilizes a defined space having a temperature maintained at or below either $M_f$ or at or above $A_f$. The thermally active device is translocated to or from one environs to another environs that is maintained or exists at an alternate temperature. As shown in FIG. 2, a catheter 20 is configured for deployment of a thermally transitioned stent 22 in a mammalian lumen 28 having stenosis 30. The stent maintains a pre-deployment form as martensite by exposure to a chilled material, which may be a fluid 24, so that the temperature is maintained at or below $M_f$. Heat is applied to the device at the transition zone 6 which adds heat to the stent alone, or to the stent and the chilled fluid, bringing both to temperature at or above $A_f$. The shape memory device (stent) may be physically advanced with a guide wire through the central lumen of the catheter. Alternately, energy associated with the transition of the device, combined with shape set geometry, creates a mechanical system, wherein force intrinsic to transition causes deployment and positioning of the transitioned stent 26 at the catheter tip.

Figure 3:
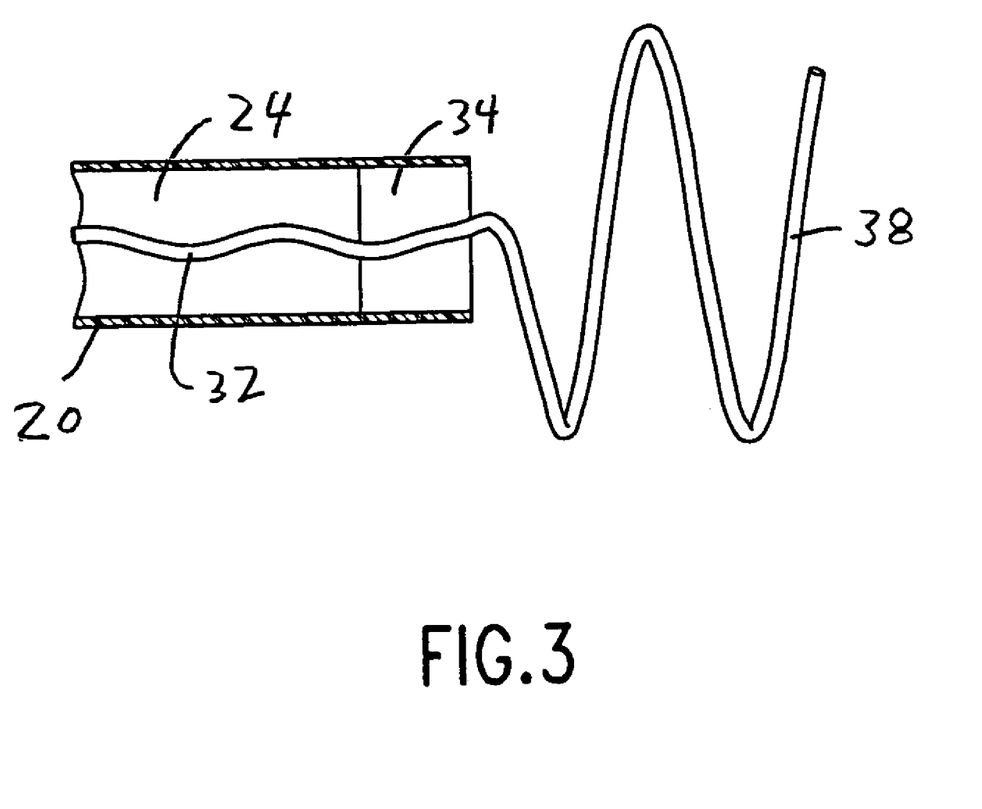
FIG. 3 is a partial, sectioned view of a shape memory device being thermally transitioned in situ.

A preferred embodiment has three substantially separate and defined temperature zones. FIG. 3. As with FIG. 2, catheter 20 placement of a tubular stent is used as an example. Shape memory device (stent) 32 is maintained in a small diameter and elongated form (martensite) prior to deployment by exposure to a chilled fluid 24. In this embodiment, the chilled fluid exits the catheter with the transitioned shape memory device 38. The chilled fluid enters into the general anatomical fluid circulation of the mammalian into which the device is being deployed. Heat applied at the defined transition zone 34 raises the temperature of the device causing transition of the device to the austenite form, and raising the temperature of the chilled fluid to maintain temperatures above $A_f$ at a zone that is beyond transition zone 34. The device is maintained in the form of a stent that is useful for its intended medical application by normal body heat.

Three differing embodiments for controlling chilled fluid are described. In each case, the shape memory device is maintained in martensite form at a temperature below $M_f$.

1. The coolant fluid flows distally from the placement catheter in a common channel occupied concurrently with the deployed shape memory device.
2. The coolant fluid flows out of the placement catheter through channels or fenestrations that are separate from that traversed by the deployed shape memory device.
3. The coolant fluid flows proximally through an alternate suction lumen that is present in the placement catheter, and the coolant fluid is removed from the deployment site utilizing a separate suction device placed parallel to the placement catheter.

As an alternate to using a chilled fluid to maintain low temperature zones, the placement device (catheter) may be constructed to contain an active cooling surface that is electrically powered. The chilled surface maintains adequate thermal communication with the shape memory device to maintain the shape memory device in martensite form.

Specific application of the preferred embodiment to stent devices or alternate function shape memory devices occurs as described herein for deployment of stent type devices. The shape memory device may be comprised of nitinol wire formed into a shape that is useful as a stent, or other specified geometrically shaped device that is introduced into a specific anatomic site in straight malleable form i.e. bendable straight wire geometry (Martensite form). Introduction as herein described is accomplished through the use of a flexible catheter. FIG. 2. This embodiment provides a heated resistance element at the tip 18 of the catheter that surrounds the nitinol wire, or formed cross-section, providing a controlled application of heat to a limited section of the nitinol element. As the shape memory device in malleable Martensite form (stent or other shaped apparatus) is translocated through the length of the resistance element or plurality of resistance elements, a transition towards the designed shape memory form (Austenite) occurs. This sequential method of placement proceeds from distal to proximal ends of the nitinol shape memory device providing for a controlled, ordered and sequential process of transition to shape memory geometry (Austenite form). The catheter tip may have an annular or helical resistance element, or plurality of elements, that are sized to maintain close contact for heat transfer to the shape memory component in a relatively narrow zone where shape and form transition of the shape memory device occurs. The resistance element is preferred to be slightly larger than the diameter of the shape memory component, so as to facilitate ease of translocation through the bore. Shape of the bore through the resistance element need not be restricted to a circular design; the bore may be shaped to maintain surface contact with any cross-sectional geometry that the nitinol element may adopt. The resistance element may take the form of multiple contact segments placed in proximity so that their simultaneous or sequential activation causes the nitinol element to transition to shape memory (the Austenite form) in a sequential and organized manner. Providing heat to obtain the transition temperature of the material in a small space, with ordered and sequential transition of the material to the deployed shape is a novel approach to transforming a shape memory stent (or other shape memory device) from a rather simple malleable shape to a more complex shape utilizing well known characteristics of shape memory alloys in readily attainable temperature transition ranges. This process may be designed and materials selected to deploy a final form that has super-elastic characteristics, or to achieve a shape that remains below final austenite temperatures, yet retains geometric form differing from the shape of the martensite component prior to placement. Spatially, a system of this size permits introduction of the stent through relatively small areas of stenosis or stricture. The small required size for access properties of this method alone offers significant advantages over current systems that require placement of a preformed stent (pre-deployment) that is nearly as large as its final deployed dimensions. It is believed that this method of placement facilitates placement of stents into anatomic locations that have heretofore been inaccessible to intervention.

Figure 4:
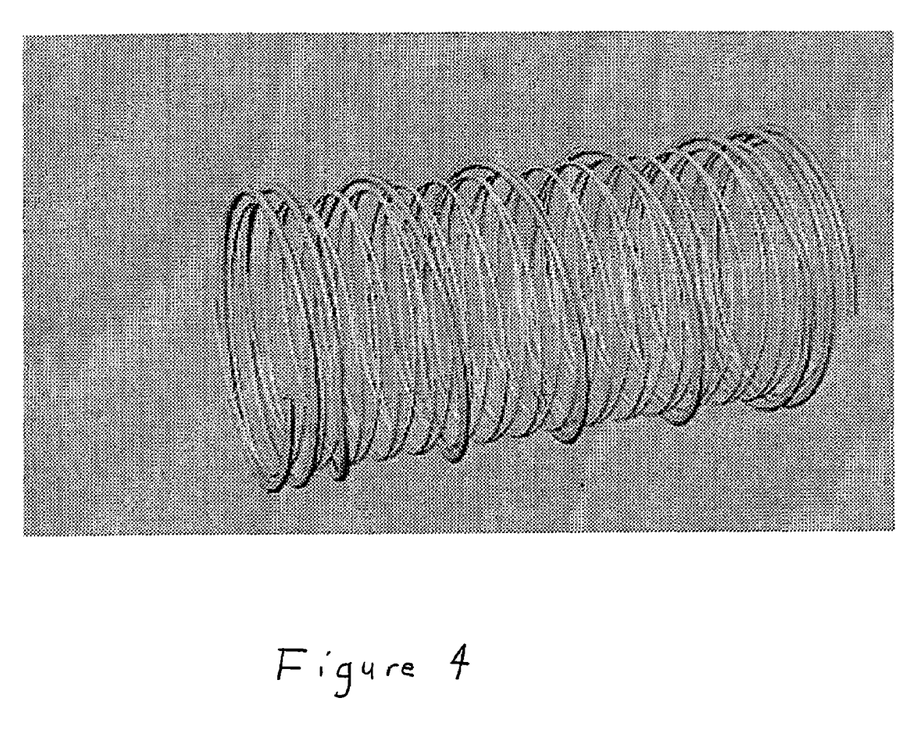
FIG. 4 is a perspective view of a helical/anti helical multiple component layered stent.

The system as designed provides for formation of relatively complex structures having variable cross-sectional size and/or shape. The final form of the stent or other formed apparatus may be of numerous shapes, with specific shape designed as required by the specific application. As shown in FIG. 3, deployment provides for structures having multiple elements deployed sequentially in a proscribed manner. A helical/anti-helical pair may be introduced through the stenosis with sequential deployment. FIG. 4. Placement of more than one helical/anti-helical pair forming a final construct with enhanced and predictable structural properties is available. Placement of multiple elements in a sequential manner allows construction of a finally deployed shape that conforms to a bifurcation of a lumen, or to hollow cavities that a single element cannot accommodate. The process of sequential deployment of multiple shape memory elements allows for sequential application of greater force to the overall structure as each additional, individual element is placed. This permits a sequenced dilation of a strictured lumen, such that as more elements are added to the construct, greater dilatation can occur until a desired dimension is realized.

Figure 5:
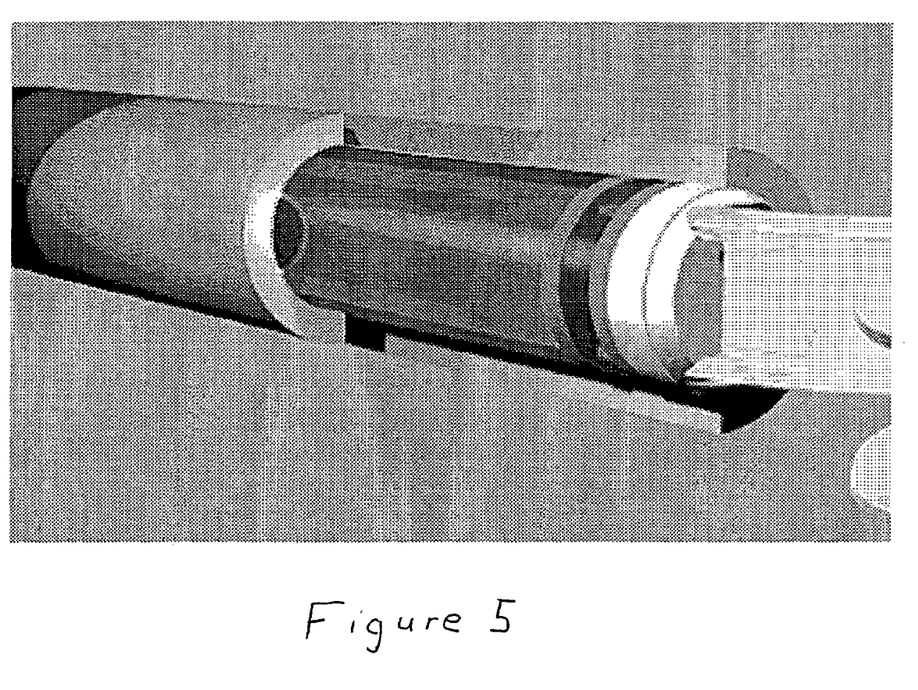
FIG. 5 demonstrates placement and deployment of a shape memory device.

A novel property of this method is the capacity to reliably heat the nitinol element to a specified temperature and predictably and completely transition the nitinol element to its final shape memory form (Austenite form) and size. The catheter is designed so that a small resistance element or plurality of resistance elements is placed near the distal tip of the catheter. Electrical current is supplied through conductors at the side walls of the catheter. This embodiment is preferred to incorporate a thermo-sensor at the distal tip capable of sensing temperature at the transition zone, and providing feedback to a controller, thus ensuring maintenance of the transition zone at a specified temperature through control of current supplied. This allows a wide range of temperatures at the transition zone. With fluid cooling, and provision of an insulated surface for the catheter tip, it is believed that temperatures in excess of 300 degrees Fahrenheit may be obtained at the transition zone without causing significant temperature rise to the external surface of the catheter, and without thermal conduction along the length of the nitinol element that could cause local tissue damage. Some embodiments of the invention provide a rigid placement device, similar to an arthroscope having a distally positioned resistance element and transition zone. FIG. 5. Thermo-sensor control and fluid cooling arrangements may be similar to those for flexible catheter applications. In applications where egress for fluid cooling medium does not enter circulation and is carried away, a suction port may be provided, so that fluid is removed as accumulation occurs.

Figure 6:
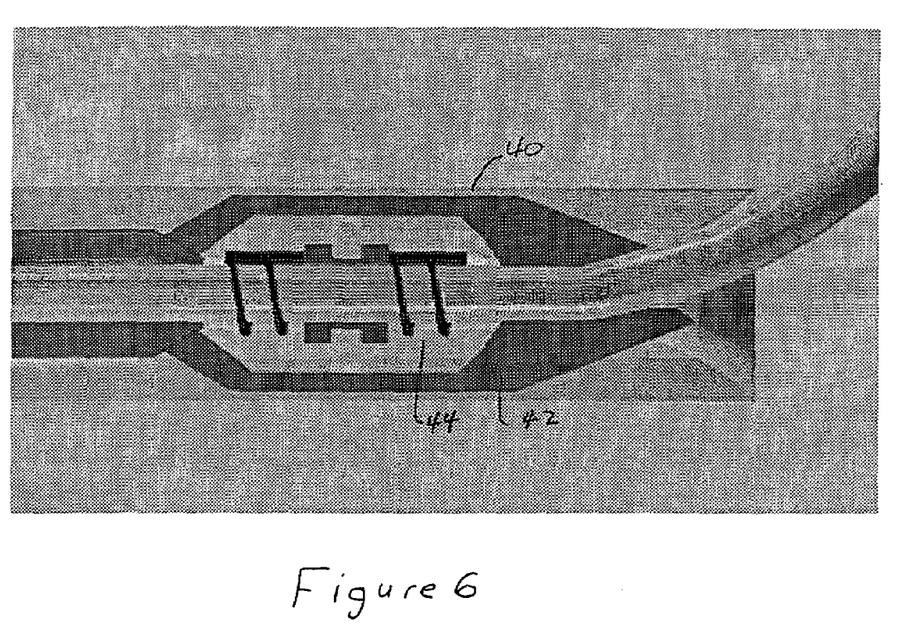
FIG. 6 is a sectioned view of a placement and deployment device.

One embodiment is a flexible catheter with a resistance element transition zone located near the distal tip of the catheter. A thermo-sensor may be provided near an insulated distal tip. Fluid cooling is provided at a distal tip for the emergent nitinol device. FIG. 6. This embodiment may be deployed through an endoscope. This embodiment includes many of the possible features of this device, but should not be construed as the sole embodiment, concept or configuration for a device capable of affecting the fundamental function of the device and method claimed herein. Other structures for providing a controlled environment for heat application in a relatively small space to a transition capable material and providing for application of heat in a sequential manner to same material, thus affecting a geometric shape change in an ordered manner with a predictable end configuration to the material, are included in the invention.

Figure 7:
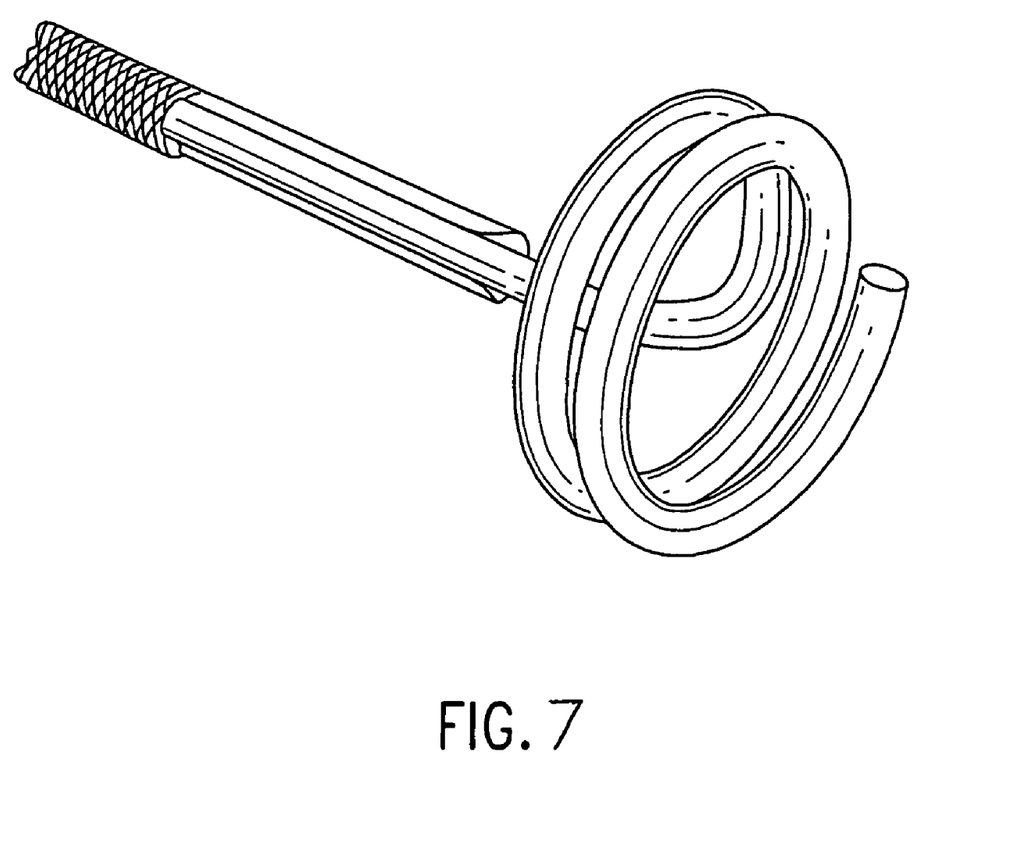
FIG. 7 is a perspective view of a helical stent transitioning and exiting a catheter.
Figure 8:
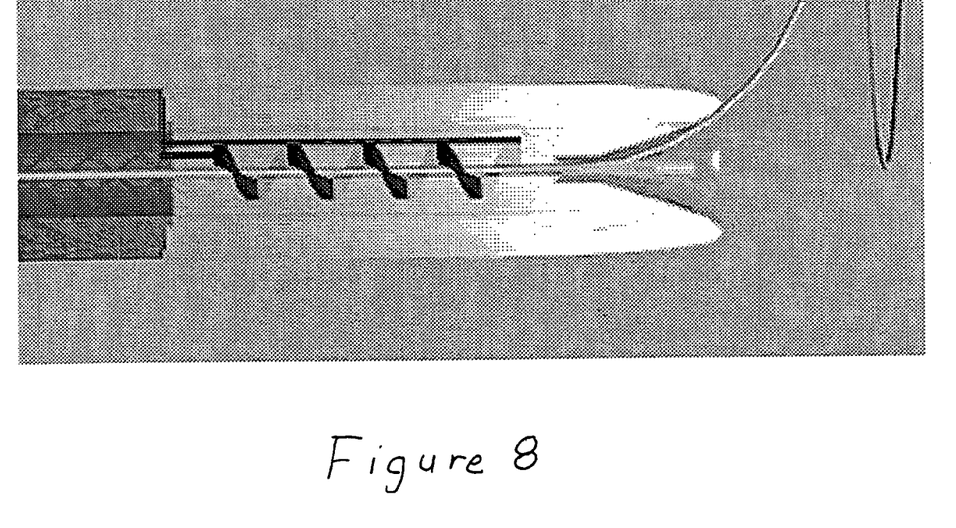
FIG. 8 is a cross section of a deployment device incorporating a resistance heating element.

The catheter may have a diameter that is slightly larger than the cross-section of the nitinol device. As an example, for a nitinol device of one millimeter in diameter, a catheter of approximately 1.8 millimeters in diameter is adequate for placement. FIG. 7. One embodiment places the device for use in Gastrointestinal Medicine applications. This method may place the flexible catheter through an operative lumen of an endoscope. The catheter is extended out of the distal tip of the endoscope under direct visualization and placed across the stenosis. Once the tip of the catheter is placed current is introduced into the resistance element circuit creating heat at the transition zone and effecting deployment of the nitinol device. The geometry of the catheter tip may be generally conical in form. A central lumen facilitates transit of the nitinol device. For applications of devices of generally helical shape the radius of curvature at the tip outlet may be slightly greater than the curvature of the helix. FIG. 8. This relationship may be exploited to cause the nitinol device to self extrude from the catheter tip. This process occurs as the nitinol device transitions to its shape memory super-elastic form (Austenite form). Force is applied against the inner surface of the very distal catheter tip, causing movement along the longitudinal axis of the nitinol device relative to the catheter.

Figure 9:
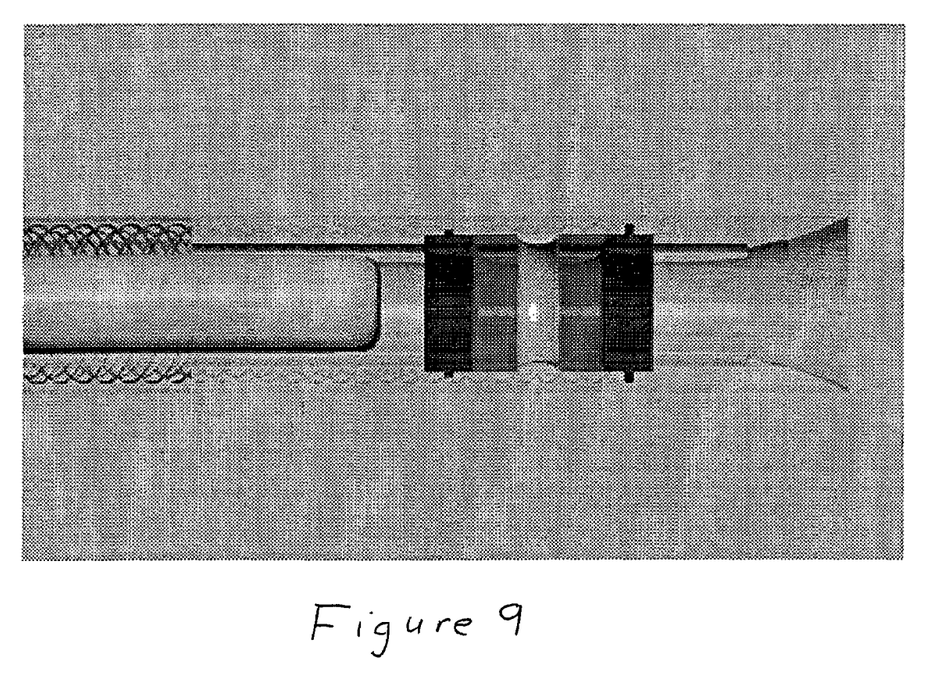
FIG. 9 is a cross section of a deployment device showing multiple resistance heat elements and a seal at the catheter tip.

The resistance element, or plurality of elements, is placed in close proximity to the distal surface of the catheter tip. FIG. 9. This specific embodiment as shown provides for three resistance heat elements and a seal at the catheter tip. The nitinol element is allowed to revolve within the portion of the catheter that is proximal to the tip and within the tip of the catheter, preventing transfer of torsional forces in the deployment process to the catheter, and minimizing the tendency of the catheter to twist during deployment. The tip 40 as shown in FIG. 6 provides for fluid cooling medium passageways 42 intrinsic to and surrounding the resistance elements 44 within the catheter tip. This embodiment provides for a nitinol temperature sensing control valve that responds to temperature changes within the transition zone. Regulation of coolant flow and maintenance of the temperature within the transition zone as desired is provided. In this embodiment, a fluid cooling medium (e.g. normal saline) is continually flushed to the tip utilizing a common lumen that contains the martensite undeployed device therein. The nitinol control valve mechanism selectively permits flow through the tip or causes a relative diversion of flow out of the catheter proximal to the tip. One embodiment provides both supply and return lumens for the fluid cooling medium, maintaining circulation, removing excess coolant and providing coolant through the tip during deployment of the nitinol apparatus. This feature is demonstrated in FIG. 5 as part of the arthroscope design. Additionally, in a configuration for vascular applications, the available circulating medium (blood) may provide adequate cooling for deployment, without a separate cooling medium required.

The methods of the invention permit construction of stents comprised of wire having variable cross-sections along their lengths, and various structural properties after deployment. Individual wires may have differing cross-sections, permitting individual components to perform differing functional tasks within a given installation. For example, a relatively stiff outer helix with widely spaced coils may be placed and followed by a much finer inner helical set with closely placed coils that functions primarily to form a wall with smaller spaces for intrusion of tissue. The resulting overall construct retains the structural properties of the outer helix having the barrier provided by the less rigid material.

Figure 10:
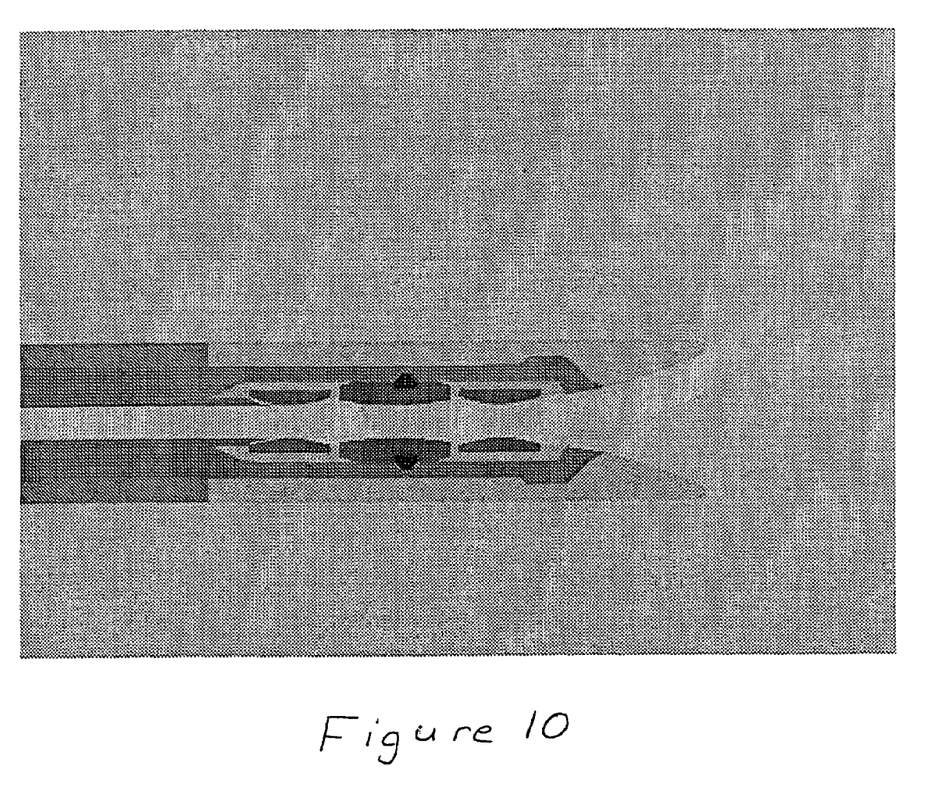
FIG. 10 is a cross section showing transition of the shape memory device by a heated fluid.
Figure 11:
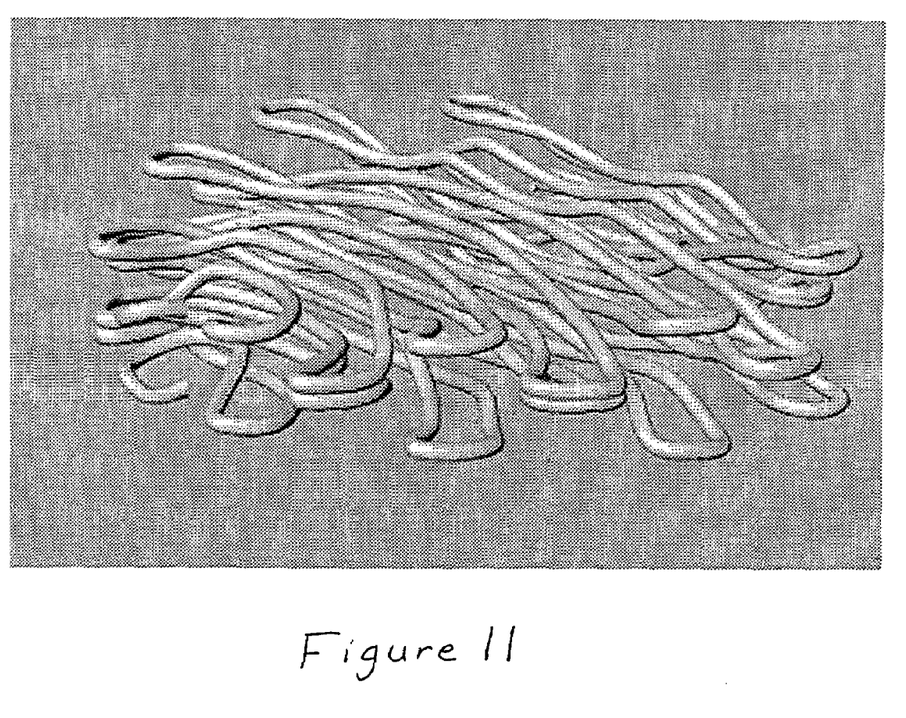
FIG. 11 is a perspective view of a device created according to the method of the inception having a complex geometry.
Figure 12:
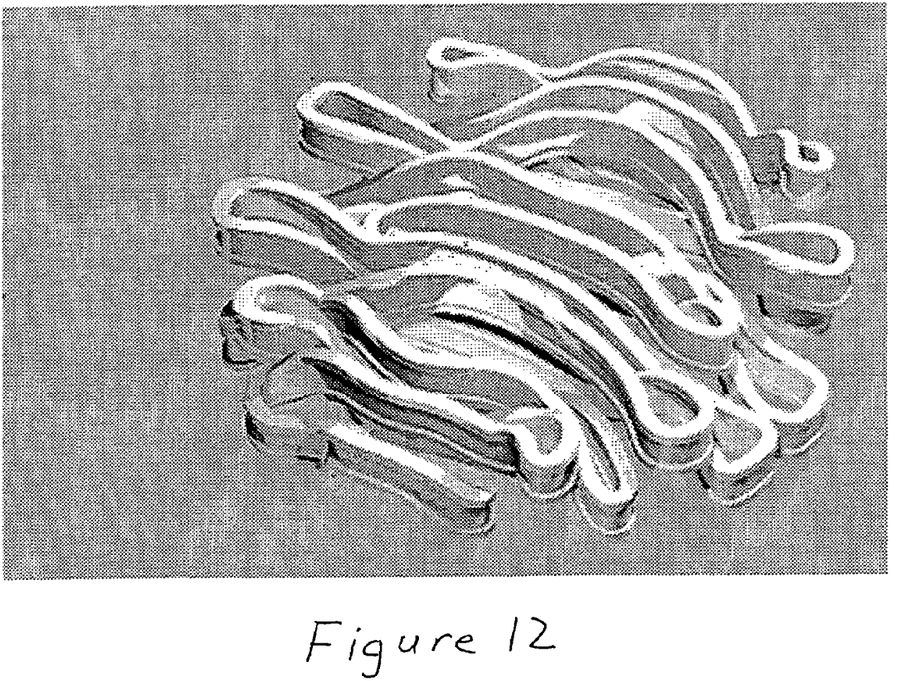
FIG. 12 is a perspective view of a device created according to the method of the inception having an irregular and complex geometry.
Figure 13:
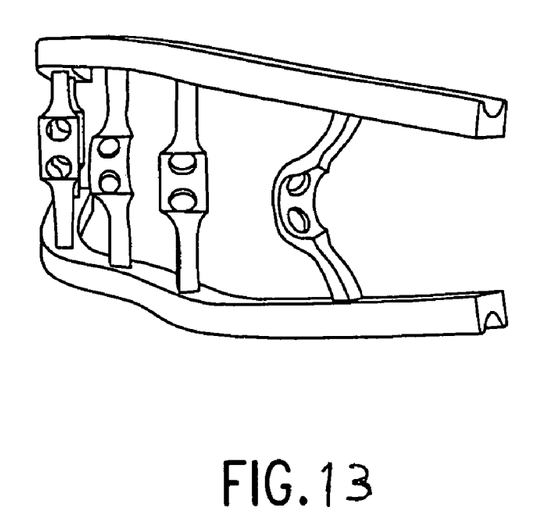
FIG. 13 is a perspective view of a device created according to the method of the inception having complex cross section.
Figure 14:
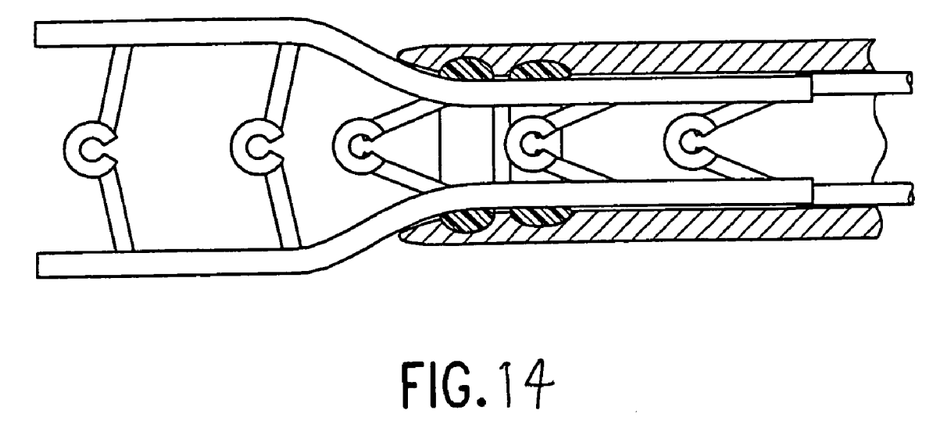
FIG. 14 is a cross section of a catheter delivering and thermally transitioning the device of FIG. 13.

Another method according to the invention uses an electrically conductive shape memory material such as nitinol as the resistance element. As shown in FIG. 10, electrical current is selectively conducted across a small segment of the stent, heating the stent and effecting transition from the martensite form to the austenite form. Activation of the stent is achieved by the application of localized heat by the resistance heat element. This method is advantageous in applications where size of the delivery apparatus is a limiting factor. Particularly in coronary artery disease, where vessel sizes are relatively small, and stents between one millimeter and three millimeters are required, utilization of a delivery catheter having the smallest possible diameter is an advantage. Direct current application with the nitinol stent as conductor/resistance element allows a correlation between energy introduced to deploy and the heat/temperature at the transition zone. There is an interrelated correlation between amperage supplied, composition of the nitinol device, cross-sectional area of the nitinol device and distance between contact points that provide a high degree of control for the transition process. Control may extend to temperatures reached at the transition zone and speed of transition from martensite to austenite forms. Empiric observation suggests that shorter conduction segments result in more rapid heating and transition, and that application of greater current likewise increases the speed of transition. Another embodiment comprises a simple single lumen deployment device (catheter) through which the martensite form of the stent is translocated. The deployment device may have a set of closely spaced contact electrodes placed distally defining a narrow transition zone. Of necessity, the stent (or other deployed apparatus) exists in a martensite form at body temperature, with transition occurring at a greater temperature at the deployment device tip with change in geometry and ultimate placement in a martensite form. This embodiment relies upon circulation of body fluids as the cooling medium for the post deployment stent. Designs that are only nominally larger than the cross-section of the deployed stent are attainable.

In one embodiment, an electrically conductive shape memory material such as nitinol functions as a resistance element by contact with electrodes at the distal end where deployment occurs. Electrode contact with the nitinol stent component is maintained through provision of an elastic system. In another embodiment a plurality of contact electrodes is arranged in a radial manner, such that the elastic members work in opposition, permitting transit of the nitinol stent component, while maintaining reliable electrical contact. The basic design of the catheter tip may be similar to the structure that utilizes the resistance heat element method of deployment, wherein provision is made for fluid cooling channels and tip curvature facilitating mechanical advantage for self deployment. Conduction of current to the contact electrodes may be provided by coaxial conductors contained within the catheter wall.

A nitinol-comprised temperature sensing valve that controls flow volume of the cooling fluid medium may be provided. FIG. 10. An annular nitinol element is in direct contact with the transition zone and controls flow through the catheter tip, and maintains desired temperature gradients between the proximal portion of the stent, transition zone, and post transition portions. As the temperature in the transition zone portion of the system increases, the nitinol annular valve element expands or contracts, affecting flow through the catheter tip. In one embodiment of this control mechanism, the valve component permits a constant minimal flow. As heat rises within the transition zone to a level that is above the target temperature, the nitinol valve device transitions, allowing greater flow through the tip, and increasing cooling at the transition zone and beyond. In an alternate embodiment, multiple flow paths provide constant flow through the catheter, with ports connected directly to an exterior to the catheter. In this embodiment, the heat sensitive nitinol valve element controls flow distally through the catheter tip and around the transition zone, while constant flow proximal to this area maintains the proximal portion of the stent at a low enough temperature to prevent transition beyond martensite form. As previously discussed, return lumens for the fluid coolant medium may be provided. Control of these ports may be controlled utilizing the temperature sensitive properties of nitinol, which regulate the temperature of those proximal portions of the stent in martensite form prior to exposure through the transition zone.

The method of the invention may be applied to sequential deployment of separate and discreet components along a common central axis or along differing axes, forming a multi-layered final construct. This structure permits separate functional characteristics to be performed by each of the layered components and increasing design functionality of the overall construct. A primary structural function may be assigned to one layer of the construct, and other functional characteristics are assigned to additional layers. This structure may provide for: formation of occlusive side walls, delivery of anti-metabolite substances, conveyance of bio-active substances including chemotherapeutic agents for localized infusion, provision of a spatially defined frame work for administration of radio-isotopes, and mechanically active functions, including peristaltic movement and valve functions.

An alternate embodiment of the layered or multiple device method uses a "Primary Stent" as the major contributing component to structural strength. A "Secondary Stent" forms an occlusive sidewall. For areas of stenosis, this structure may be the most common functions required.

The Primary Stent may be a single helix. In a preferred embodiment, the Primary Stent is a set of four paired helix/anti-helix pairs with single elements of 0.3 mm nitinol shape memory wire. Transition temperatures with $A_f$ less than 37 degrees Celsius are specified, and an ideal $A_f$ is 35 degrees Celsius. Additionally, $M_f$ temperatures of greater than 4 degrees Celsius are specified. These transition temperatures allow deployment into the human body at reasonable temperatures, and maintenance of the device in a super-elastic state after deployment.

A preferred embodiment permits deployment through a "Thermal Method Catheter" which maintains the device at temperatures less than $M_f$ within the length of the catheter. This is accomplished with circulated chilled fluid bathing the pre-deployment device. Heat is introduced at the tip of the catheter, bringing the stent and chilled fluid to temperatures greater than $A_f$. As the device is heated there is near instantaneous transition to the austenite super-elastic form with assumption to the shape set geometry. Mechanical force generated as transition occurs causes the stent to extrude outwardly from the catheter tip. This process allows for precisely controlled placement of the distal tip of the stent device, since a specified segment of the stent engages the lumen side walls at a point in time, which in this instance the distal end of the stent.

The Primary Stent comprising geometry of helical/anti-helical pairs may be collapsed to a small diameter in the martensite form. For the specific device of this embodiment, four helical/anti-helical pairs with each linear element 0.3 mm in diameter may be collapsed to a diameter of 1.3 mm prior to deployment. After deployment, the diameter of this stent is specified at 8 mm. Stenting devices may be specified according to the size and structure required to meet specific anatomic requirements.

The size specifications permit tortuous deformation of the stent device during placement. Since the device is in martensite form prior to transition at the catheter tip, the mechanical force required to achieve deformation is much less than would be required to deform an equivalently sized and shaped device in austenite form.

A function of the Primary Stent is dilatation of a stenotic lumen, and ultimately, contribution to the structural characteristics of the final construct comprised of multiple deployed stent components. This characteristic allows optimization of design of the individual components to meet specific structural or physiologic functions without the inherent compromises required to meet multiple functions within a single component.

In a preferred embodiment, the Secondary Stent provides an occlusive sidewall. In this embodiment, the Secondary Stent is deployed utilizing the thermal method through a catheter. The Secondary Stent is of composite construction having a shape memory helical structure embedded within a polymer tubular occlusive sidewall. The helical shape memory components have a primary and secondary helical form. The primary helix is coiled and has loops that protrude through the outside surface of the polymer tube. Upon transition and placement of the Secondary Stent, the protruding loops of shape memory material engage the wire helix/anti-helix structure of the Primary Stent, and secure a spatial relationship between the components.

In this embodiment, both the Primary Stent and the Secondary Stent may have their lengths adjusted at the time of placement. The nitinol shape memory elements of the preferred embodiment have been sized to allow cutting of the structural element in situ. The polymer portion of the Secondary Stent likewise may be transected utilizing a knife and anvil type apparatus.

Another embodiment comprises discontinuous super-elastic elements that are coated with an elastic polymer. Once sufficient length of the material is positioned, the extrusion process is halted. Torsion stress is applied along the placement axis, affecting separation through shear of the elastic coating at predetermined discontinuous segments of the super-elastic components. The coating polymer may be configured to provide an occlusive sidewall, or allow fenestrations to provide a permeable side wall.

Both the Primary and Secondary Stent may be removed or repositioned during placement by reversal of the thermal transition process at the catheter tip. For repositioning of a stent element, control of the proximal portion of the device by maintaining tension along the long axis of the device during the deployment process can overcome transition force causing a reversal of deployment. Removal of previously positioned devices is achieved by grasping the proximal portion of the device while flooding the area of placement with a chilled fluid. The device may then be withdrawn through a tapered catheter tip, with the environment internally chilled. The device may be removed after it is contained within the catheter.

In another embodiment, a thermal billiary stenting system is a two component system. Certain physical attributes are realized with the use of two components having differing forms and physical properties. The first component placed is referred to herein as the "Primary Stent." The Primary Stent affords minimal diameter in the pre-deployment form. This physical attribute is obtained from the use of a helix/anti-helix pair or pairs. The geometric pair(s) may be extended longitudinally in a manner analogous to a Chinese finger trap, providing an overall maximal cross-sectional dimension that is approximately twice the diameter of a single wire component. Cross-sectional diameters of less than 1.5 mm in the pre-deployment form may be achieved.

In addition to minimization of diameter, the Primary Stent provides structural strength for the overall two component construct. The structural characteristics of the Primary Stent are realized upon transition to its shape memory super-elastic form. Relatively high hoop strength for this component may substitute for mechanical dilatation heretofore obtained using a balloon catheter, thus affecting dilatation of the strictured or obstructed region of the billiary tract. The relatively small pre-deployment size of the primary stent allows for passage of the apparatus (stent and deployment catheter) across the obstruction prior to activation of the deployment process.

The second component of the system is referred to as the "Inner Core Stent". The Inner Core Stent is placed subsequent to the Primary Stent, which has opened, and defines a lumen of varied composition and function. In one embodiment, the Inner Core Stent comprises a fine weave of thermally active nitinol mesh in tubular form. The Inner Core Stent is deployed in manner that is analogous to the Primary Stent. The Inner Core Stent occupies the inner lumen of the Primary Stent and forms a semi-permeable side wall. The Inner Core Stent is designed to interlock with, or is otherwise secured relative to, the Primary Stent to preclude dislodging. Micro motion of the Inner Core Stent relative to the primary stent may be controlled by the attachment structure of the components.

Variable length capabilities are afforded by construction of the two components in a structurally segmented manner. The shape memory portions of each stent component are discontinuous, with small intervening segments comprising material(s) that are easily disrupted, allow separation to occur at any given segment, and creating the opportunity for length adjustment to meet individual patient requirements.

It is not necessary that the multiple components comprising the final construct are of the same length, nor is necessary for there to be a complete overlap relative to length of the two or more placed components. These attributes allow the system to be varied to suit particular stenting requirements and differing structural or physiologic requirements.

The invention has advantages over prior stents where there are limitations in placement due to degree of stenosis, relative inaccessibility to convoluted path of access, size of lumen, or placement site being subject to forces that will deform a malleable structure. Potential application sites include: the billiary duct system, coronary arterial circulation, carotid circulation, peripheral vascular sites, cerebral circulation, esophagus and bowel, the urinary tract, and gynecologic sites. Tissue expanders used in plastic surgery, conformal delivery devices for radiation treatment, and localized delivery of anti-metabolites in chemotherapy. Designs are not limited to solid cross-sections, particularly where introduction of therapeutic agents is best accomplished in a staged manner, or through a treatment schedule. Devices according to the invention may be configured to provide for a lumen or plurality of lumens facilitating introduction and or removal of specific therapeutic agents. Stents according to the invention may be applied at any anatomic site where currently available stents are applied, and sites that have been previously inaccessible are now accessible.

Constructs according to the heat activated transition method of the invention include highly varied geometric structures having varied functions and sites of application. FIGS. 11, 12, 13 and 14. The nitinol apparatus can perform functions of previously available stents: maintenance of lumen patency, opening of stenosis or stricture, and providing structural support. Additionally, the apparatus may provide a carrier mechanism for application of therapeutically active substances including: anti-metabolites, anti-microbials, cytotoxic agents, or radioactive components. The ability to place a conforming apparatus into a hollow viscous, or of a corresponding geometry to a solid mass or organ, provides an opportunity to maintain localized therapeutic agents in proximity or within the substance of specific diseased organs and affect a purely local effect. Additionally, due to the superelastic properties of austenite forms of the material, the geometries of therapeutic shape memory devices may be so designed that as a therapeutic effect is realized (i.e. involution of a tumor) the device may change in shape and size to continuously maintain approximation of the therapeutic agent to its target.

Shape memory devices may be made from shape memory materials, including, but not limited to, thermoplastic, polymers, and alloys such as nitinol or ferrous alloys having shape memory properties. The specific shape memory material selected will depend on the application for the device. The application of heat or withdrawal of heat in the transition zones will depend upon the shape memory material used.

What is claimed is:

1. A method of sequentially transitioning a thermally active shape memory device, comprising the steps of:
    progressively translocating said thermally active shape memory device through a first temperature zone of a lumen comprising said first temperature zone;
    progressively translocating said thermally active shape memory device through a controlled temperature zone of said lumen, wherein said first temperature zone and said controlled temperature zone are at materially different temperatures; and
    progressively and sequentially thermally transitioning a geometric change in shape of said thermally active shape memory device at said controlled temperature zone as said shape memory device is progressively translocated through said lumen as a result of thermal transfer between said shape memory device and said lumen at said controlled temperature zone of said lumen,
    wherein the progressive and sequential thermal transitioning of the geometric change in shape of said thermally active shape memory device progressively and sequentially produces a shape transitioned thermally active shape memory device.

2. A method of sequentially transitioning a thermally active shape memory device as described in claim 1, wherein said transitioned thermally active shape memory device is in situ and is in position for use when said transitioned thermally active shape memory device exits said controlled temperature zone of said lumen.

3. A method of sequentially transitioning a thermally active shape memory device as described in claim 1, wherein the method of claim 1 is performed in situ.

4. A method of sequentially transitioning a thermally active shape memory device as described in claim 1, wherein said first temperature zone and said controlled temperature zone are maintained in said lumen in thermal separation from each other, wherein no material thermal communication between said first controlled temperature zone and said additional temperature zone occurs.

5. A method of sequentially transitioning a thermally active shape memory device as described in claim 1, said first temperature zone of said lumen is a relatively lower temperature zone and said controlled temperature zone of said lumen is a relatively higher temperature zone.

6. A method of sequentially transitioning a thermally active shape memory device as described in claim 1, said first temperature zone of said lumen is a relatively higher temperature zone and said additional controlled temperature zone of said lumen is a relatively lower temperature zone.

7. A method of sequentially transitioning a thermally active shape memory device as described in claim 1, wherein the method of claim 1 is performed in situ in a mammalian.

8. A method of sequentially transitioning a thermally active shape memory device as described in claim 1, further comprising the steps of:
    introducing heat from a heating element to controlled temperature zone; and
    variably controlling a temperature of said controlled temperature zone by variably controlling the introduction of said heat from said heating element.

9. A method of sequentially transitioning a thermally active shape memory device as described in claim 1, further comprising the steps of introducing electrical current from an element comprising electrical contacts that transmit electrical current to said thermally active shape memory device, wherein said thermally active shape memory device has properties of electrical resistance;
    increasing a temperature of said thermally active shape memory device by application of said electrical current to said thermally active shape memory device; and
    progressively and sequentially thermally transitioning a geometric change in shape of said thermally active shape memory device by said application of said electrical current as said thermally active shape memory device is translocated through said lumen to produce said transitioned thermally active shape memory device.

10. A method of sequentially transitioning a thermally active shape memory device as described in claim 1, further comprising the step of introducing a chilled material into said controlled temperature zone, wherein a temperature of said thermally active shape memory device is maintained or reduced by transfer of heat between said thermally active shape memory device and said chilled material as said thermally active shape memory device is translocated through said controlled temperature zone of said lumen.

11. A method of sequentially transitioning a thermally active shape memory device as described in claim 1, further comprising the step of deploying said thermally active shape memory device by the application of mechanical force to said thermally active shape memory device and changing a geometric shape of said thermally active shape memory device.

12. A method of sequentially transitioning a thermally active shape memory device as described in claim 1, wherein said thermally active shape memory material is substantial linear in shape in said first temperature zone of said lumen and prior to entering said controlled temperature zone.

13. A method of sequentially transitioning a thermally active shape memory device as described in claim 1, wherein said thermally active shape memory material progressively and sequentially transitions in shape to said shape transitioned thermally active shape memory device in said lumen, and said thermally active shape memory device is progressively and sequentially transitioned out of said lumen after each portion of the thermally active shape memory device is shape transitioned.

14. A method of sequentially transitioning a thermally active shape memory device as described in claim 1, wherein said thermally active shape memory material is substantial linear in shape in said first temperature zone of said lumen and prior to entering said controlled temperature zone, and wherein said thermally active shape memory material progressively and sequentially transitions in shape to said shape transitioned thermally active shape memory device at said controlled temperature zone of said lumen, and said thermally active shape memory device is progressively and sequentially transitioned out of said lumen after each portion of the thermally active shape memory device is shape transitioned.

* * * * *